(12) United States Patent
Hughes et al.

(10) Patent No.: US 7,941,209 B2
(45) Date of Patent: May 10, 2011

(54) SIGNAL ANALYSIS METHOD

(75) Inventors: Nicholas Hughes, Oxford (GB); Lionel Tarassenko, Oxford (GB); Stephen Roberts, Oxford (GB)

(73) Assignee: OBS Medical Limited, Abingdon (GB)

( * ) Notice: Subject to any disclaimer, the term of this patent is extended or adjusted under 35 U.S.C. 154(b) by 1176 days.

(21) Appl. No.: 11/579,834

(22) PCT Filed: May 6, 2005

(86) PCT No.: PCT/GB2005/001747
§ 371 (c)(1),
(2), (4) Date: Nov. 7, 2006

(87) PCT Pub. No.: WO2005/107587
PCT Pub. Date: Nov. 17, 2005

(65) Prior Publication Data
US 2008/0140403 A1      Jun. 12, 2008

(30) Foreign Application Priority Data

May 7, 2004      (GB) .................................. 0410248.9

(51) Int. Cl.
A61B 5/044      (2006.01)
A61B 5/0476      (2006.01)
A61B 5/0488      (2006.01)

(52) U.S. Cl. ...................................... 600/523; 600/509

(58) Field of Classification Search .................. 704/242, 704/256, 256.1, 256.7; 600/509, 523
See application file for complete search history.

(56) References Cited

U.S. PATENT DOCUMENTS

| | | |
|---|---|---|
| 5,663,929 A | 9/1997 | Pavone et al. |
| 5,737,489 A | 4/1998 | Chou et al. |
| 5,778,881 A | 7/1998 | Sun et al. |
| 2002/0049593 A1 | 4/2002 | Shao |

FOREIGN PATENT DOCUMENTS

GB      2347253      8/2000

OTHER PUBLICATIONS

International Search Report for PCT/GB2005/001747 mailed Jan. 19, 2006.
Rabiner, "Tutorial on Hidden Markov Models and Selected Applications in Speech Recognition", Proceedings of the IEEE, 77:257-286 (1989).
Hughes et al., "Markov Models for Automated ECG Interval Analysis", Advances in Neural Information Processing Systems 16, MIT Press, (2004).
Thoraval et al., "Continuously Variable Durations Hidden Markov Models for ECG Segmentation", Proceedings IEEE-EMBS, pp. 529-530 (1992).

(Continued)

*Primary Examiner* — Carl H. Layno
*Assistant Examiner* — Tammie K Heller
(74) *Attorney, Agent, or Firm* — Taft Stettinius & Hollister LLP

(57) ABSTRACT

Improvement in the reliability of segmentation of a signal, such as an ECG signal, is achieved through the use of duration constraints. The signal is analysed using a hidden Markov model. The duration constraints specify minimum allowed durations for specific states of the model. The duration constraints can be incorporated either in the model itself or in a Viterbi algorithm used to compute the most probable state sequence given a conventional model. The derivation of a confidence measure from the model can be used to assess the quality and robustness of the segmentation and to identify any signals for which the segmentation is unreliable, for example due to the presence of noise or abnormality in the signal.

6 Claims, 11 Drawing Sheets

OTHER PUBLICATIONS

Ghahramani et al., "Factorial Hidden Markov Models", Machine Learning, vol. 29(2) (1997).

Freund et al., "Regression Analysis", Academic Press, Chapter 2 only (1998).

Hughes et al., "Automated QT Interval Analysis with Confidence Measures", Computers in Cardiology, 31:765-768 (2004).

Coast et al., "An Approach to Cardiac Arrhythmia Analysis Using Hidden Markov Models", IEEE Transactions on Biomedical Engineering, vol. 37(9):826-835 (1990).

Ajmera et al., "Speech/Music Segmentation Using Entropy and Dynamism Features in a HMM Classification Framework", Speech Communication, vol. 40(3):351-363 (2003).

Laurila, "Noise Robust Speech Recognition with State Duration Constraints", IEEE International Conference on Munich, vol. 2:871-874 (1997).

Gupta et al, "Using Phoneme Duration and Energy Contour Information . . . ", Speech Processing 2, VLSI, Underwater Signal Processing, Toronto, May 14-17, 1991, International Conference on Acoustics, Speech & Signal Processing, ICASSP, New York, IEEE, U.S., vol. 2 Conf. 16, Apr. 14, 1991, pp. 341-344; XP010043891.

Vaseghi, "State duration modelling in hidden Markov models", Signal Processing, Elsevier Science Publishers B.V. Amsterdam, NL, vol. 41, No. 1, Jan. 1995, pp. 31-41; XP004014180.

Kim et al, "HMM with Global Path Constraint in Viterbi Decoding for Isolated Word Recognition", Proceedings of the International Conference on Acoustics, Speech, and Signal Processing (ICASSP). Speech Processing 1. Adelaide, vol. 1, Apr. 19, 1994, pp. I-605; XP000529435.

Burshtein, "Robust Parametric Modeling of Durations in Hidden Markov Models", IEEE Transactions on Speech and Audio Processing, IEEE Service Center, New York, vol. 4, No. 3, May 1996, pp. 240-242, XP000800777.

Jiang, "Confidence Measures for Speech Recognition: A survey", Speech Communication, Elsevier Science Publishers, Amsterdam, NL, vol. 45, No. 4, Apr. 2005, pp. 455-470, XP004823829.

SIGNAL ANALYSIS METHOD

CROSS REFERENCE TO RELATED APPLICATION

This application is the US national phase of international application PCT/GB2005/001747 filed 6 May 2005, which designated the U.S. and claimed priority of GB 0410248.9 filed 7 May 2004, the entire contents of each of which are hereby incorporated by reference.

BACKGROUND OF THE INVENTION

The invention concerns a method for the analysis of a signal. The analysis may comprise automated segmentation of a signal, such as an electrocardiogram (ECG) or other biomedical signal, into its constituent waveform features, optionally together with the derivation of an associated confidence measure indicating the accuracy and robustness of the segmentation, through the use of a hidden Markov modelling technique incorporating duration constraints.

The ECG (also known by the acronym EKG) is an important non-invasive signal which measures the electrical activity of the heart. Each individual heartbeat is comprised of a number of distinct cardiological stages, which in turn give rise to a set of distinct features in the ECG waveform. These features represent either depolarization (electrical discharging) or repolarization (electrical recharging) of the muscle cells in particular regions of the heart. FIG. 1 shows a human ECG waveform and the associated features. The standard features of the ECG waveform are the P wave, the QRS complex and the T wave. Additionally a small U wave (following the T wave) is occasionally present.

The cardiac cycle begins with the P wave (the start and end points of which are referred to as $P_{on}$ and $P_{off}$), which corresponds to the period of atrial depolarization in the heart. This is followed by the QRS complex, which is generally the most recognisable feature of an ECG waveform, and corresponds to the period of ventricular depolarization. The start and end points of the QRS complex are referred to as the Q and J points. The T wave follows the QRS complex and corresponds to the period of ventricular repolarization. The end point of the T wave is referred to as $T_{off}$ and represents the end of the cardiac cycle (presuming the absence of a U wave).

By examining the ECG signal in detail it is possible to derive a number of informative measurements from the characteristic ECG waveform. These can then be used to assess the medical condition of the patient and detect any potential abnormalities present in the cardiac rhythm.

A particularly important measurement is the "QT interval", which is defined as the time from the start of the QRS complex to the end of the T wave, i.e. $T_{off}$–Q. This timing interval corresponds to the total duration of electrical activity (both depolarization and repolarization) in the ventricles.

The QT interval is especially significant since a longer than normal interval is a good indicator of Long QT Syndrome (LQTS). This is a potentially fatal condition that renders sufferers vulnerable to a very fast, abnormal heart rhythm (an arrhythmia) known as "torsade de pointes". When this rhythm occurs the heart is unable to beat effectively and the blood flow to the brain falls dramatically. The result is a sudden loss of consciousness and possible cardiac death.

Another important measure is the PR interval, which is defined as the time from the start of the P wave to the start of the QRS complex, i.e. Q–$P_{on}$. This corresponds to the time from the onset of atrial depolarization to the onset of ventricular depolarization, and can be used to detect conditions such as atrioventricular block.

In addition to the measurement and assessment of the QT and PR intervals, the accurate and robust segmentation of the ECG waveform into its constituent features is also important for detecting conditions such as ST elevation, and for computing the heart rate by locating the peak of the QRS complex (known as the R point) in successive heart beats.

Given the aforementioned importance of accurately determining the feature boundaries in the ECG waveform, a great deal of effort has therefore been expended to automate this process. Initial work in this area focused on classical signal processing and pattern recognition approaches such as thresholding and template matching. More recently, statistical approaches based on hidden Markov models (HMMs) have been applied to the problem of ECG segmentation.

In hidden Markov modelling there is an underlying state sequence of interest that cannot be observed directly. In addition however, there is also a signal or observation sequence that is probabilistically related to this state sequence, and from which we would like to infer the most probable value of the given state sequence.

At the heart of hidden Markov models are two probabilistic functions, one of which relates the probability of the state of interest at a particular time step given the value of this state at the previous time step, and another which relates the probability of a signal or observation value given the particular state value.

The hidden Markov modelling approach is particularly suitable for ECG analysis because it makes use of the unique statistical characteristics of the ECG waveform features. In addition, the model can also take advantage of the sequential nature of the waveform features (i.e. T wave follows QRS complex which follows P wave), which helps to improve the segmentation of noisy ECG signals.

Unfortunately, one significant drawback with hidden Markov models is that they are prone to producing highly unreliable segmentations. These segmentations are characterised by segmented features that typically last only a few time samples. This problem stems from a bias of the model towards features with a very short duration, and therefore makes standard HMMs unsuitable for applications such as ECG segmentation that require a high degree of robustness.

FIG. 2 and FIG. 4 show two sample ECG waveforms together with the waveform boundaries as determined by an expert ECG analyst (solid vertical lines) and those inferred using a standard hidden Markov model (dashed vertical lines). In both instances the model finds two QRS complexes, and two T waves, when there is only one of each present in the original signal. In particular, the model segmentation includes a very short QRS complex and T wave, which occur directly after the start of the P wave and before the true QRS complex location. Such "double-beat" segmentations severely impact upon the performance and reliability of the model.

SUMMARY OF THE INVENTION

With this background in mind, one object of the present invention is concerned with improving the reliability of the segmentation of signals, such as ECG signals.

A further aim of the invention is the derivation of a confidence measure from the model. This confidence measure can be used to assess the quality and robustness of the segmentation, and detect any ECG waveforms that are either too noisy, or sufficiently unusual, such that a reliable segmentation by an automated system is not possible.

According to one aspect of the invention there is provided a computer-implemented method for bio-medical signal segmentation using a hidden Markov model, the model comprising a plurality of states, the method comprising the steps of:

specifying a minimum duration constraint $d_{min}$ for at least one of the states;

for each state in the model with a specified minimum duration, replacing the state by a set of sub-states, with the total number of sub-states equal to the value of the minimum duration constraint $d_{min}$;

connecting together the set of sub-states to form a left-right Markov chain, wherein the first $d_{min}-1$ sub-states each have a self-transition probability of zero, a transition probability of one of transitioning to the state immediately to their right, and a transition probability of zero of transitioning to any other state in the model; and applying the model to data representing the biomedical signal to obtain information on the segmentation of the signal into the states.

According to another aspect of the invention there is provided a computer-implemented method for segmenting a signal, comprising a sequence of observations, into a sequence of states of a finite state discrete time Markov process using a modification to the Viterbi algorithm, the modification comprising:

defining a duration variable and a duration constraint for at least one state of the finite state discrete time Markov process incorporated into the Viterbi algorithm, the duration constraint specifying the minimum duration for said at least one state;

applying the modified Viterbi algorithm to the signal to compute the most probable duration-constrained state sequence which accounts for the sequence of observations; wherein at each time step in the computation of the most probable state sequence for each state in the finite state discrete time Markov process which accounts for the sequence of observations up to that time step and ends in said state:

for each state having a duration constraint, using the duration variable for that state to keep track of the length of the consecutive sequence of predecessor states which are comprised only of that state and end in that state at the previous time step;

if the duration variable for that state is greater than or equal to the specified duration constraint for that state, then transitions from that state to any other given state in the Markov process are considered in the state sequence computations at the given time step;

if the duration variable for that state is less than the specified duration constraint for that state, then transitions from that state to any other state in the Markov process are not considered in the state sequence computations at the given time step; and following the computation of the set of most probable state sequences up to the given time step and ends in a particular state, updating the duration variable for each state having a duration constraint in order to keep track of the length of the consecutive sequence of predecessor states which are comprised only of that particular state and end in that state at the time step just considered.

A further aspect of the invention provides a computer-implemented method for analysing a signal which has been segmented according to a probabilistic segmentation algorithm, the method comprising:

calculating a confidence measure for each of a plurality of segmented signal features;

plotting the confidence measures against the respective segmented signal feature lengths;

applying density modelling techniques to determine a suitable region of the data space associated with high confidence features;

determining whether the confidence measure for a specific signal feature falls outside this region.

BRIEF DESCRIPTION OF THE DRAWINGS

Embodiments of the invention will now be described, by way of example only, with reference to the accompanying drawings in which:—

DETAILED DESCRIPTION OF THE INVENTION

Figure 1:
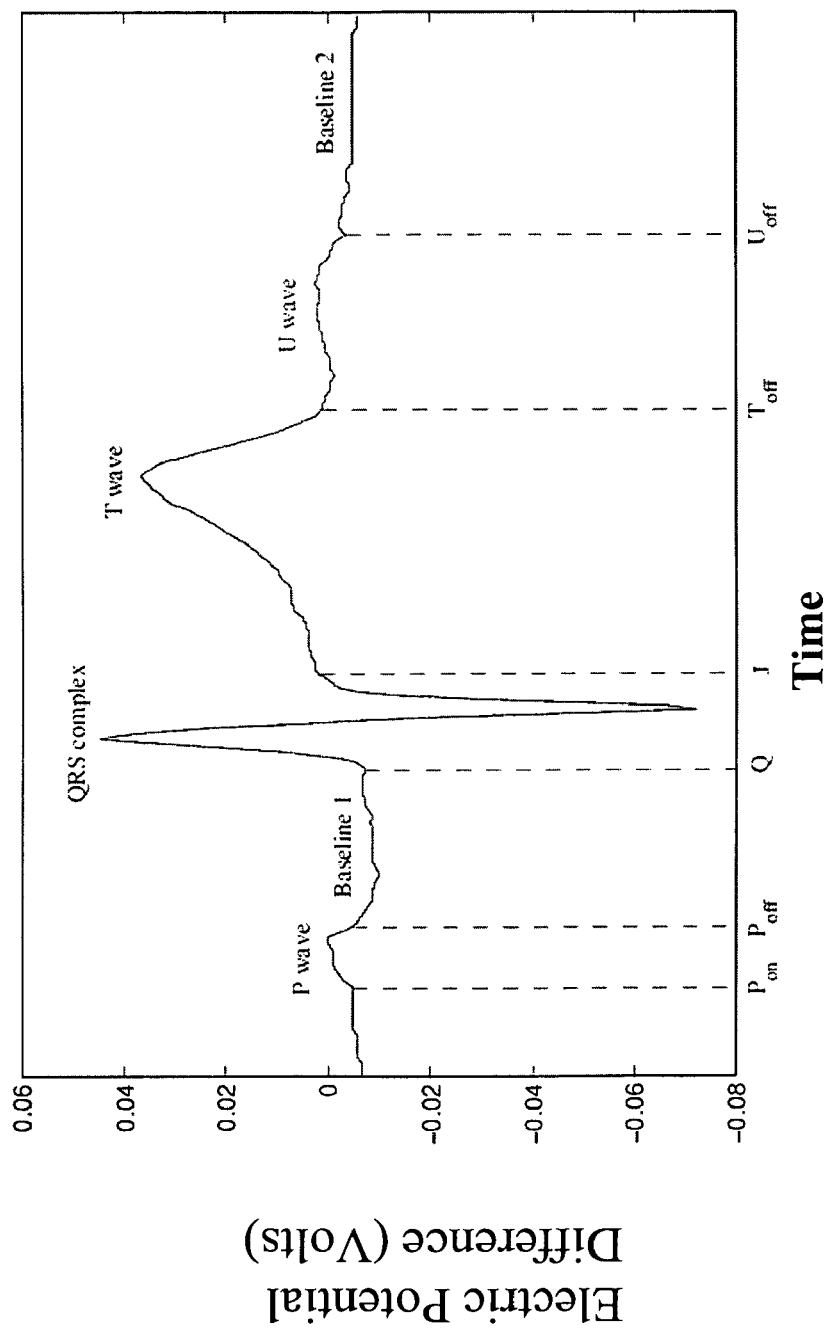
FIG. 1 shows a fully labelled ECG waveform.
Figure 7A:
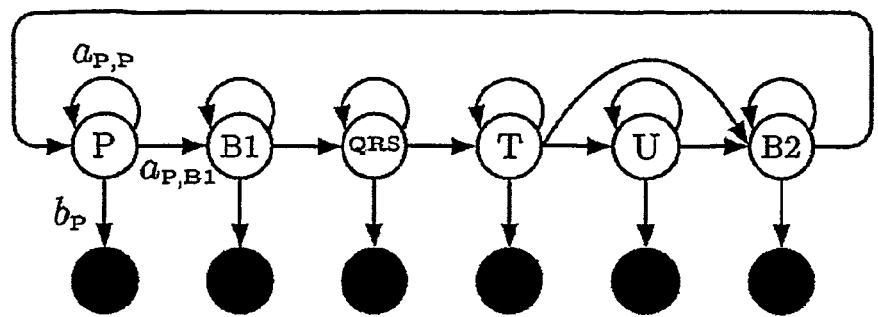
FIG. 7a shows the architecture of a standard hidden Markov model for segmenting an ECG signal into a P wave region, a baseline region, a QRS complex region, a T wave region, an optional U wave region, and a second baseline region. In addition, the transition probabilities α and the observation model probability distribution b for the P wave state are indicated.
Figure 7B:
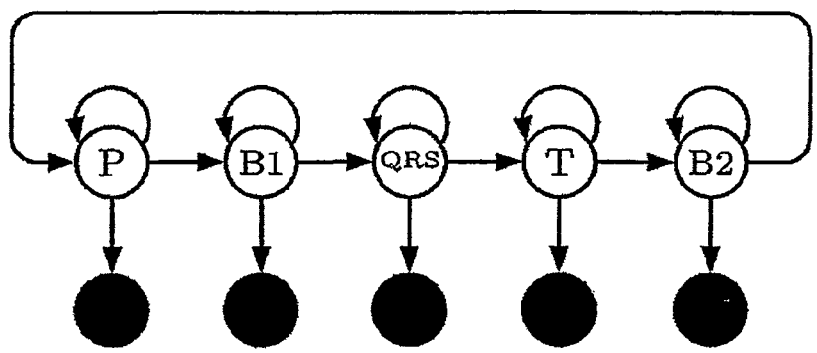
FIG. 7b shows the architecture of a standard hidden Markov model for segmenting an ECG signal in a similar manner to the model of FIG. 7a, but without an optional U wave region.
Figure 7C:
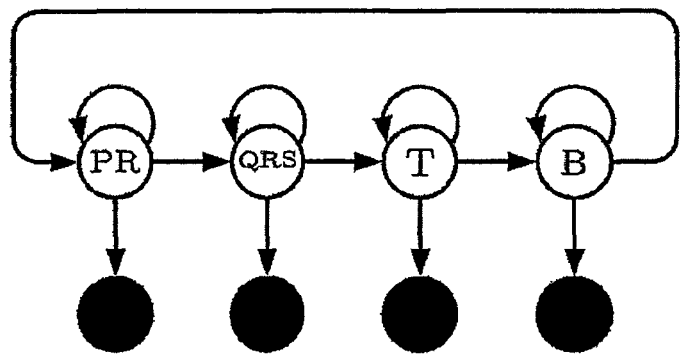
FIG. 7c shows the architecture of a standard hidden Markov model for segmenting an ECG signal into a PR interval region, a QRS complex region, a T wave region, and a baseline region.
Figure 7D:
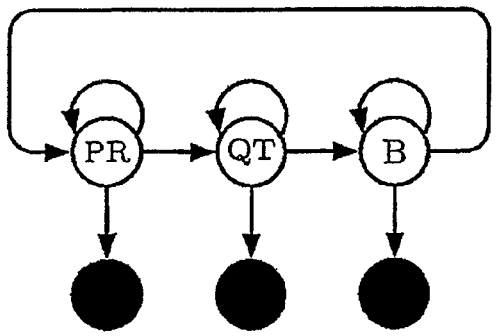
FIG. 7d shows the architecture of a standard hidden Markov model for segmenting an ECG signal into a PR interval region, a QT interval region, and a baseline region.
Figure 7E:
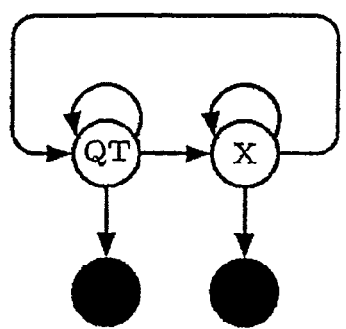
FIG. 7e shows the architecture of a standard hidden Markov model for segmenting an ECG signal into a QT interval region, and a second region (X) corresponding to the remainder of the signal.

The following embodiments of the invention are based on the foundation of a hidden Markov model (HMM) that is trained to recognise one or more of the features of an ECG signal. The model is comprised of a plurality of states, each of which represents a particular region of an ECG signal. A graphical depiction of the architecture or "topology" of one form of hidden Markov model for ECG segmentation is shown in FIG. 7a. This model is comprised of six unique states, which represent in turn—the P wave, the section of baseline between the end of the P wave and the start of the QRS complex (termed "Baseline 1"), the QRS complex, the T wave, the U wave, and the section of Baseline between the end of the T wave (or U wave if one is present) and the start of the P wave of the following heart beat. These sections of the ECG waveform are indicated in FIG. 1. A number of alternative forms of hidden Markov model architecture for ECG segmentation are depicted in FIG. 7b-7e. In each case the model is comprised of a "hidden" state sequence (indicated by the clear nodes), which is stochastically related to an observed signal (indicated by the shaded nodes). For ECG segmentation the hidden state $s_t$ corresponds to the particular waveform feature which is active at time t, and the observed signal sample $O_t$ corresponds to the associated signal sample of the ECG waveform.

The model is governed by the following three parameters: i.) the initial state distribution $\pi$, ii.) the transition matrix A, and iii.) the observation probability models $b_k$ for each state k in the HMM. Training an HMM involves adjusting these parameters in order to minimise a specific error function.

Given an appropriate set of values for the model parameters, the HMM takes the form of a generative probability model for the ECG signal. More precisely, the model defines a stochastic procedure for generating ECG waveforms. This procedure begins with the selection of an initial state, which is achieved by sampling from the initial state distribution $\pi$. The particular initial state selected then corresponds to the first waveform feature of the ECG signal (i.e. the feature which is active at time sample t=1). The associated ECG signal sample for this waveform feature is then produced by sampling from the corresponding observation probability model $b_k$ for that particular state.

The next stage in the procedure is to stochastically choose the next model state, i.e. the waveform feature which is active at time sample t=2. This is achieved by sampling from the transition matrix. This matrix takes the form of a simple table that defines, for every state in the model, the probability of the next state occurring. Once the next state has been chosen in this manner, the model then generates the associated ECG signal sample by sampling from the appropriate observation probability model. This procedure iterates successively for the remaining time steps.

Given a particular ECG signal, segmenting the signal into the various features or regions of interest defined by the model architecture (i.e. locating the signal boundaries of each of the model states) involves reversing the aforementioned "generating procedure". Thus, the aim is to infer the most probable sequence of the hidden states that gave rise to the given ECG signal. This state sequence then defines the boundaries of the regions of interest in the ECG signal, and thus the corresponding segmentation.

This segmentation procedure can be achieved through the use of the Viterbi algorithm. More precisely, the Viterbi algorithm takes as inputs a given ECG signal together with a trained hidden Markov model, and returns the most probable hidden state sequence, as described in L R Rabiner, "A Tutorial on Hidden Markov Models and Selected Applications in Speech Recognition", *Proceedings of the IEEE,* 77:257-286, 1989.

For the model to perform successfully on the task of segmenting ECG waveforms, it is necessary to use a robust and informative encoding of the ECG. A particularly effective representation is the set of coefficients from an undecimated wavelet transform (UWT) of the ECG signal, as described by N P Hughes, L Tarassenko and S J Roberts in "Markov Models for Automated ECG Interval Analysis", *Advances in Neural Information Processing Systems* 16, MIT Press, 2003.

Once the representation for the ECG has been chosen, training the HMM involves adjusting the parameters of the model in order to maximise the probability (or likelihood) of the ECG data, i.e. $p(O|\lambda)$, where O represents the dataset of ECG signals and $\lambda$ represents the set of HMM parameters. Training can be achieved in either a supervised or an unsupervised fashion.

With supervised learning, the training data consists of a number of ECG waveforms together with the corresponding state labels. Thus for each signal sample $O_t$ from a given ECG waveform, we also have available a label $l_t$ that indicates which particular state (i.e. waveform feature) the sample belongs to. The initial state distribution and the transition matrix can then be computed using the following maximum likelihood estimates:

$$\pi_i = m_i / N$$

$$a_{ij} = n_{ij} / \sum_k n_{ik}$$

where $m_i$ is the total number of times that the first signal sample (over all the ECG waveforms) belongs to state i, $n_{ij}$ is the total number of transitions from state i to state j in all of the label sequences, and N is the number of individual ECG signals in the data set.

The observation probability models $b_k$ for each state k can be learnt by extracting all of the signal samples belonging to that particular state and then fitting the observation model to those samples directly. For a Gaussian observation model this simply involves computing the mean and variance of the given samples. For a Gaussian mixture model it is necessary to use the EM algorithm (Expectation-Maximization algorithm) in order to learn the parameters of the observation model from the given samples.

With unsupervised learning, the training data consists of the ECG waveforms only. The hidden Markov model can then be trained using the Baum-Welch algorithm (which is a particular instance of the more general EM algorithm).

In order to prevent the model from producing unreliable segmentations, embodiments of the invention impose a set of duration constraints upon the model. These constraints restrict the ability of the model to infer segmentations that are physiologically implausible (in terms of the duration of the associated waveform features).

In particular, the duration constraints take the form of a single number $d_{min}$ for each state in the model, which represents the minimum permitted duration for that particular state (in "samples"). These duration constraints can be estimated in a number of different ways. If labelled ECG data is available, the duration constraint for each waveform feature can simply be estimated as a suitable fraction of the minimum duration of that feature present in the data set. For example, the minimum T wave duration could be set to 80% of the minimum T wave duration present in the data set.

If labelled data is not available, and we only have the raw ECG signals to work with, then the duration constraints must be learnt from the data. This can be achieved by using the trained model to segment the ECG signals in the data set, and then estimating the duration constraints from the resulting segmentations (in a similar fashion to that previously described for labelled data). In this case it is first necessary to remove any unreliable "double-beat" segmentations that would otherwise impact upon the quality of the estimated duration constraints.

Once the duration constraints have been computed, they can then be used to improve the segmentation performance of the hidden Markov model. This can be achieved by either incorporating the duration constraints into the Viterbi algorithm, or by incorporating the duration constraints into the HMM architecture. Both these methods will now be considered in detail.

The Viterbi algorithm is the key inference procedure that enables hidden Markov models to be used successfully in practice, as detailed in L R Rabiner, "A Tutorial on Hidden Markov Models and Selected Applications in Speech Recognition", *Proceedings of the IEEE*, 77:257-286, 1989. In the context of ECG analysis, the Viterbi algorithm allows us to locate the most likely boundary positions (i.e. onsets and offsets) for the P wave, QRS complex and T wave, in a given ECG waveform.

In order to incorporate duration constraints into the Viterbi algorithm, it is necessary to restrict the state sequence returned by the algorithm such that the duration of each of the associated waveform features obeys the given duration constrains.

More formally, given an HMM $\lambda$ (with K states) and an ECG signal $O=O_1 O_2 \ldots O_T$, we would like to infer the most probable state sequence $S=s_1 s_2 \ldots s_T$ which satisfies the duration constraints $d_{min}(k)$ for $k=1 \ldots K$. Each duration constraint embodies the requirement that the duration of any "run" of state k must be at least $d_{min}(k)$ samples. The aim therefore is to ensure that we do not infer any state sequences that we know a priori to be invalid (with respect to the duration of the individual state runs).

The standard Viterbi algorithm is based upon an efficient procedure for computing the likelihood of the most probable state sequence that accounts for the first t observations and ends in state i:

$$\delta_t(i) = \max_{s_1 s_2 \ldots s_{t-1}} p(s_1 s_2 \ldots s_t = i, O_1 O_2 \ldots O_t | \lambda)$$

At the heart of the algorithm is the following recurrence relation for computing $\delta_t(i)$:

$$\delta_t(i) = \max_j \{\delta_{t-1}(j) a_{ji}\} b_i(O_t)$$

which makes use of the fact that the state sequence is first-order Markov (i.e. we need only consider the previous state in our computation of $\delta_t(i)$). At any time t then, it is always possible for the most probable path through the state trellis to transition from its current state to a different state, provided that the associated transition probability is non-zero. Thus in order to incorporate duration constraints into the Viterbi algorithm, this path must be restricted such that any transition from one state to another is only permitted if the current state of interest has been occupied for an amount of time greater than or equal to the minimum permitted duration.

The duration constrained Viterbi algorithm according to this first embodiment of the invention proceeds as follows. At each time step t of the recursion we keep track of the duration d(i) of the current "run" of state i which ends at time t−1. More precisely, the duration variable for each state is used to keep track of the length of the consecutive sequence of predecessor states that are comprised only of that particular state and end in that state at the previous time step. If this duration is greater than or equal to the minimum permitted duration $d_{min}(i)$, we consider transitions from this state to any other state j when computing $\delta_t(j)$ (as with the standard Viterbi recurrence). However if the current state occupancy is less than the minimum permitted, transitions from this state to different states are not allowed and the state can only self-transition (until its minimum duration constraint is satisfied). Once $\delta_t(i)$ has been computed for all values of t, the standard backtracking method can be used to produce the final state sequence.

Figure 6:
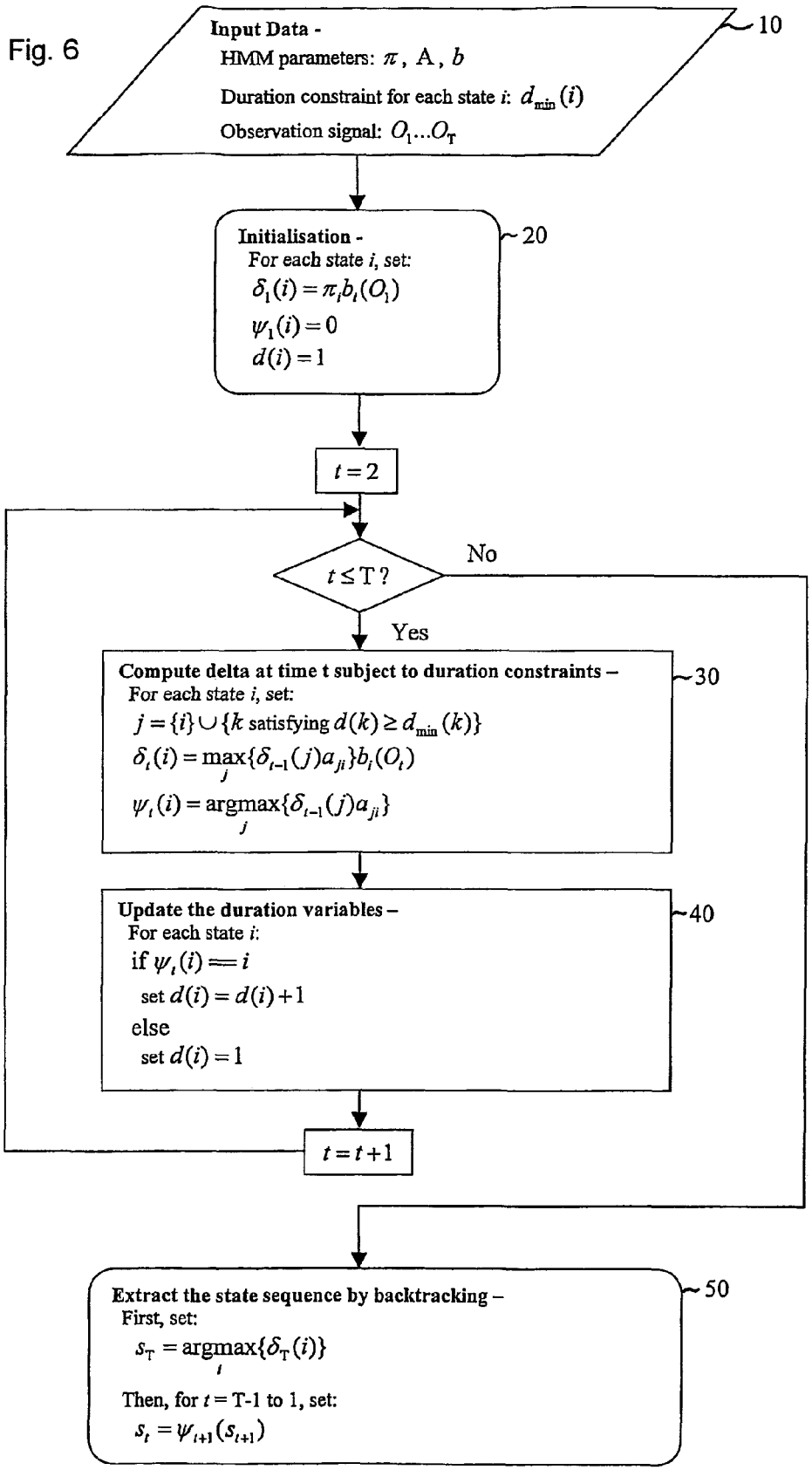
FIG. 6 is a flow chart detailing the operation of the new duration constrained Viterbi algorithm.

The overall procedure of the duration constrained Viterbi algorithm is illustrated schematically in the flow chart in FIG. 6. The first stage of the algorithm is the input of the HMM parameters, the observed signal, and the minimum duration constraint for each state. This is illustrated in box 10.

The next stage of the algorithm, depicted in box 20, concerns the initialisation of the variables of interest. More precisely, for each state i we set $\delta_1(i)=\pi_i b_i(O_1)$, $\psi_1(i)=0$ and d(i)=1. In common with the standard Viterbi procedure, the variable $\psi_t(i)$ is used to store the most likely state at time t−1, given that the model was in state i at time t. The variable d is unique to the duration-constrained Viterbi procedure, and is used to keep track of the duration of the current "run" of each state ending at time sample t−1. More precisely, for each state i the duration variable d(i) is used to keep track of the length of the consecutive sequence of predecessor states that are comprised only of state i and end in state i at time step t−1.

The main body of the duration constrained Viterbi algorithm is shown in boxes 30 and 40. These two procedures are iterated in succession for all time samples from 2 to T (where T is the length of the signal). Box 30 computes the value of $\delta_t(i)$ and $\psi_t(i)$ for each state i at the given time step t. In the standard Viterbi algorithm, the "max" and "argmax" operators used in the computation of $\delta_t(i)$ and $\psi_t(i)$ respectively, are evaluated for all possible previous states (from 1 to K). However in the duration constrained Viterbi algorithm these operators are only evaluated for those states that satisfy their minimum duration constraint $d_{min}$. In addition the operators are also evaluated for the current state i, such that the most likely previous state is always allowed to be the state we are currently considering.

Given this, the first step of box 30 therefore is to compute the set of states j (including state i by default) that satisfy their minimum duration constraints, i.e. those states k satisfying $d(k) \geq d_{min}(k)$. The computation of $\delta_t(i)$ and $\psi_t(i)$ is then evaluated for this set of states j only.

The next stage in the duration constrained Viterbi algorithm is to update the duration variable for each state. More precisely, if the most likely previous state $\psi_t(i)$ is also state i, then the duration variable for this state is incremented by 1, i.e. d(i)=d(i)+1. This corresponds to the case of a "self-transition"—where the model remains in the same state for successive time steps, and therefore causes the duration of the current "run" of state i ending at time sample t to increase by one. However if the most likely previous state $\psi_t(i)$ is not state i, then the duration variable for this state is reset to one, i.e. d(i)=1. This corresponds to the case of a transition from a different state into state i, and therefore ends the current "run" of state i self-transitions.

Once boxes 30 and 40 have been computed up to and including time sample T, the standard Viterbi backtracking procedure can be used to extract the most probable state sequence using the previously computed $\delta$ and $\psi$ variables. The first step in this backtracking procedure, as illustrated in box 50, is to find the state that maximises the value of $\delta_T$, i.e. $s_T = \mathrm{argmax}_i \{\delta_T(i)\}$. Once this value has been computed, the most probable state at the preceding time step (i.e. T−1) can be found simply from the value of $\psi_T(s_T)$. Using this recursive procedure, the most probable state values can then be computed for all the remaining time samples.

According to a second embodiment of the invention, an alternative way of improving the segmentation performance of the HMM is to incorporate the duration constraints directly into the model architecture. Once the constraints have been incorporated in this way, the standard Viterbi algorithm can then be used to infer the optimal duration constrained segmentation of a given ECG waveform.

Incorporating the duration constraints into the HMM architecture involves replacing each state in the model with a set of $d_{min}$ new states. These states are connected in a simple left-right fashion and share a common observation density.

More precisely, for each state k with a minimum duration of $d_{min}(k)$ (where $d_{min}(k) > 1$), we augment the model with $d_{min}(k) - 1$ additional states directly preceding the original state k. Each additional state has a self-transition probability of zero, a transition probability of one of transitioning to the state immediately to its right, and a transition probability of zero of transitioning to any other state in the model. Thus taken together these states form a simple left-right Markov chain, where each state in the chain is only occupied for at most one time sample (during any run through the chain).

The most important feature of this chain is that the parameters of the observation probability model for each state are identical to those of the original state k. This sharing of model parameters is generally referred to as "tying". Thus the observations associated with the $d_{min}$ new states replacing the original state k are governed by the same set of parameters as the original state.

Figure 8:
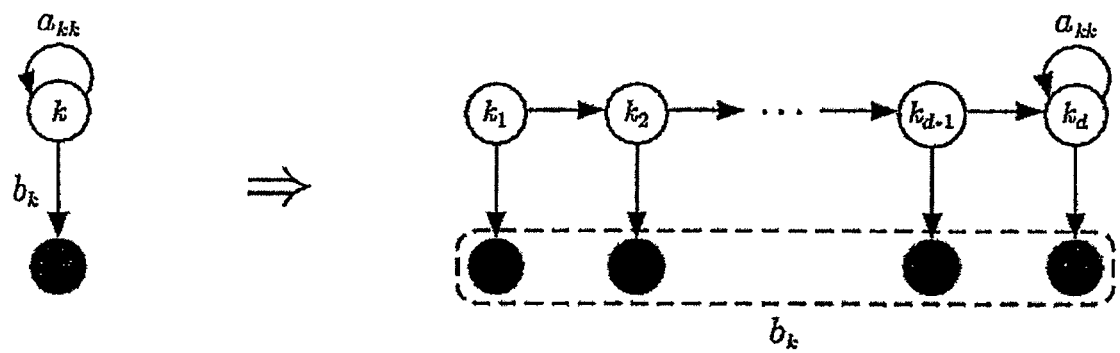
FIG. 8 shows a graphical illustration of incorporating a duration constraint into a hidden Markov model.

The overall procedure for incorporating duration constraints into the HMM architecture is illustrated graphically in FIG. 8. On the left of the figure is one of the states from the original hidden Markov model architecture (as depicted in FIG. 7). On the right of the figure is the new structure that this state is transformed into through the incorporation of the duration constraints. In particular, $d_{min}(k) - 1$ new states (without self-transition loops) are connected to the original state in a simple left-right manner, and the parameters of the observation probability models for these states are "tied" to the corresponding parameters of the original state. This latter procedure is indicated by the dashed box in the figure.

Figure 9:
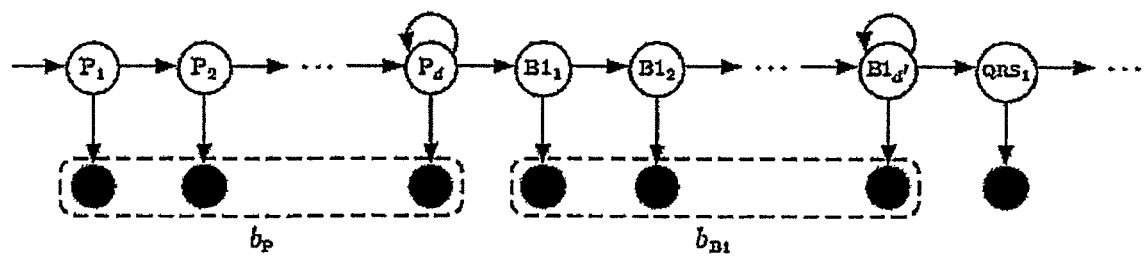
FIG. 9 shows part of the architecture of a hidden Markov model employing built-in duration constraints for ECG segmentation.

The aforementioned process is repeated for each of the original states in the original hidden Markov model (i.e. P, B1, QRS, T etc.). Thus the overall effect of incorporating duration constraints into the model architecture is that each original single state in the model is replaced by a new "duration-constrained" structure. FIG. 9 shows part of the resulting duration-constrained HMM architecture. Each waveform feature in the model (e.g. P wave, QRS complex etc.) is now associated with a plurality of states. This plurality then encapsulates the minimum duration requirement for each ECG waveform feature.

Once the duration constraints have been incorporated into the HMM in the manner previously described, the model can then be used to segment new ECG waveforms using the standard Viterbi algorithm. The resulting segmentations are then guaranteed to obey the duration constraints since the model is no longer able to generate state sequences whose duration is less than that permitted.

Figure 2:
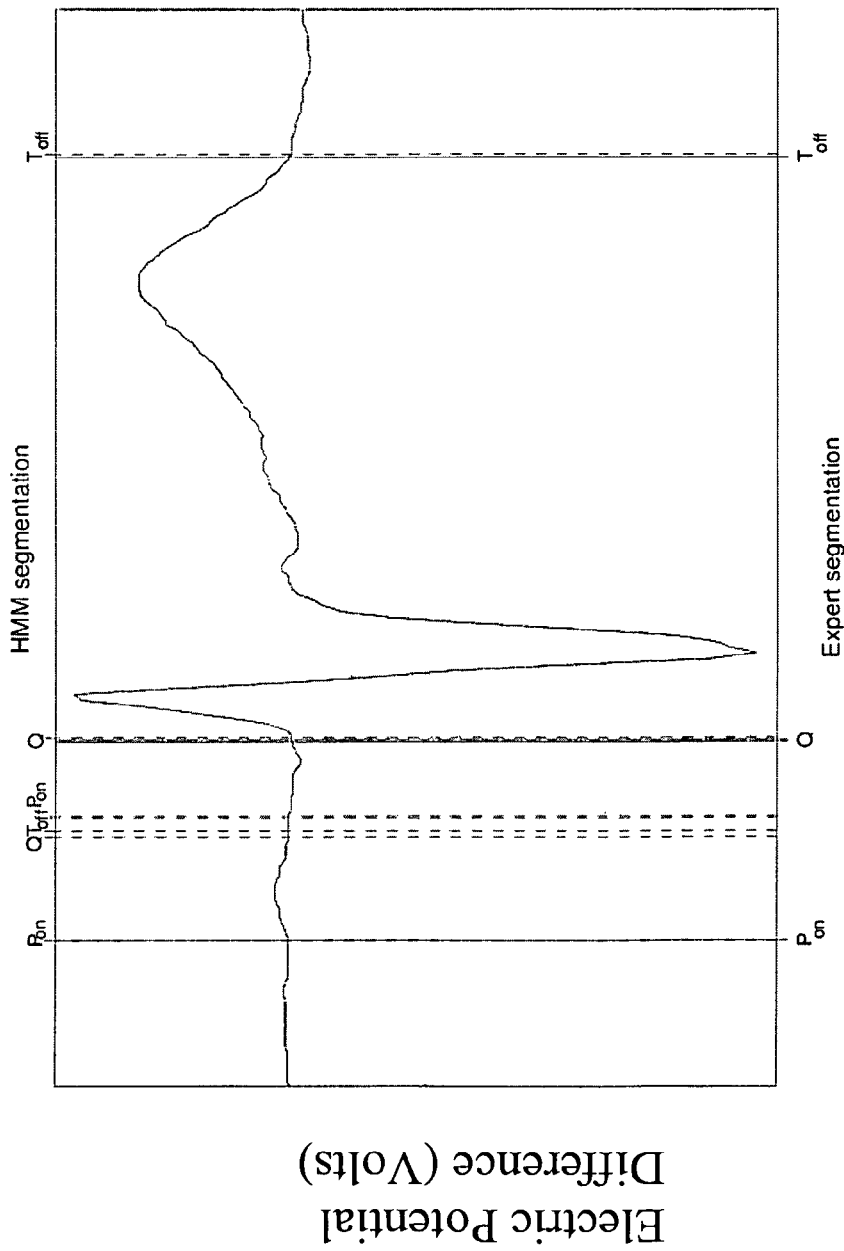
FIG. 2 shows an ECG waveform together with the waveform boundaries as determined by an expert ECG analyst, and those inferred using a standard hidden Markov model approach.
Figure 3:
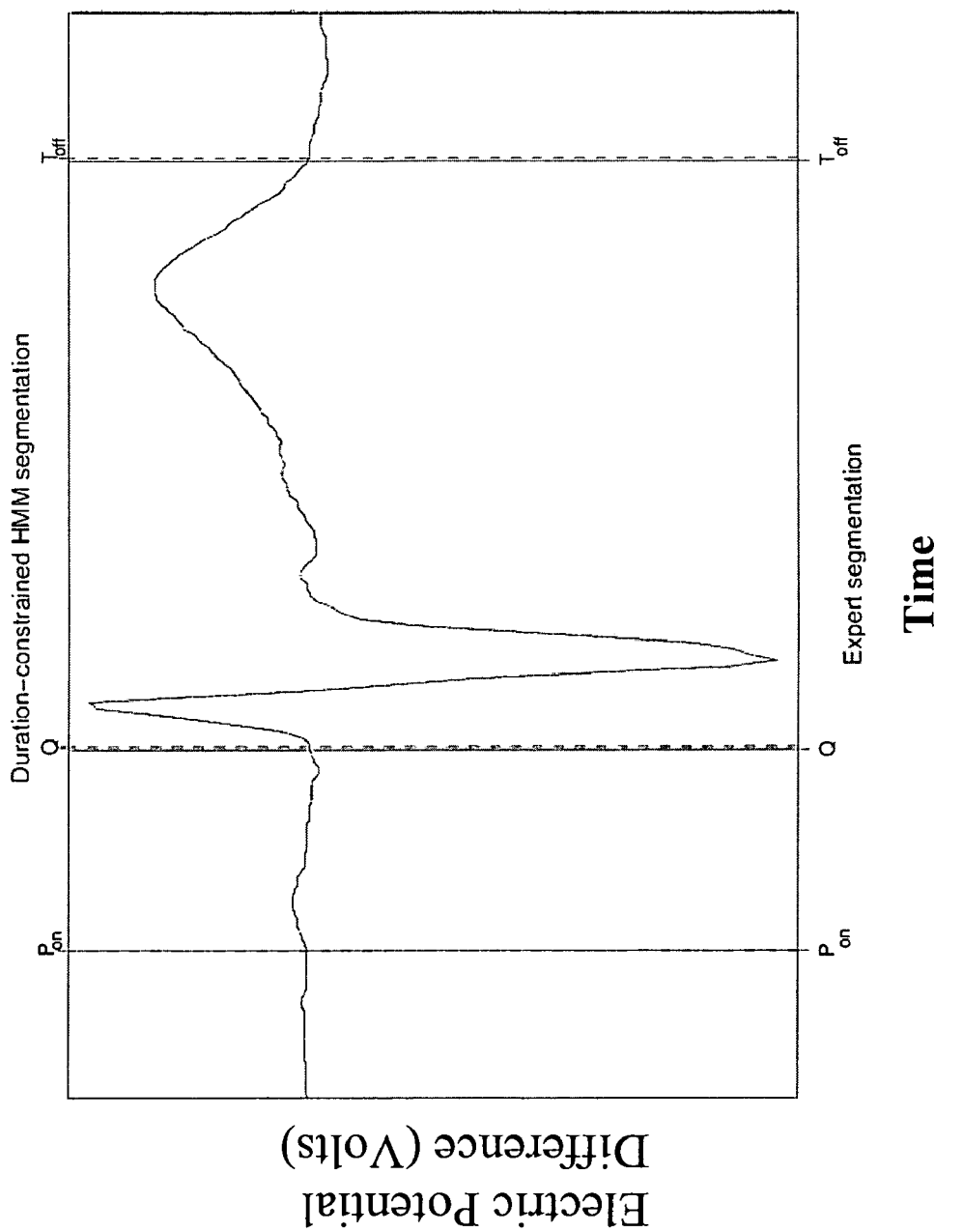
FIG. 3 shows the same ECG waveform as used in FIG. 2, together with the waveform boundaries as determined by an expert ECG analyst, and those inferred using the new duration-constrained approach.
Figure 4:
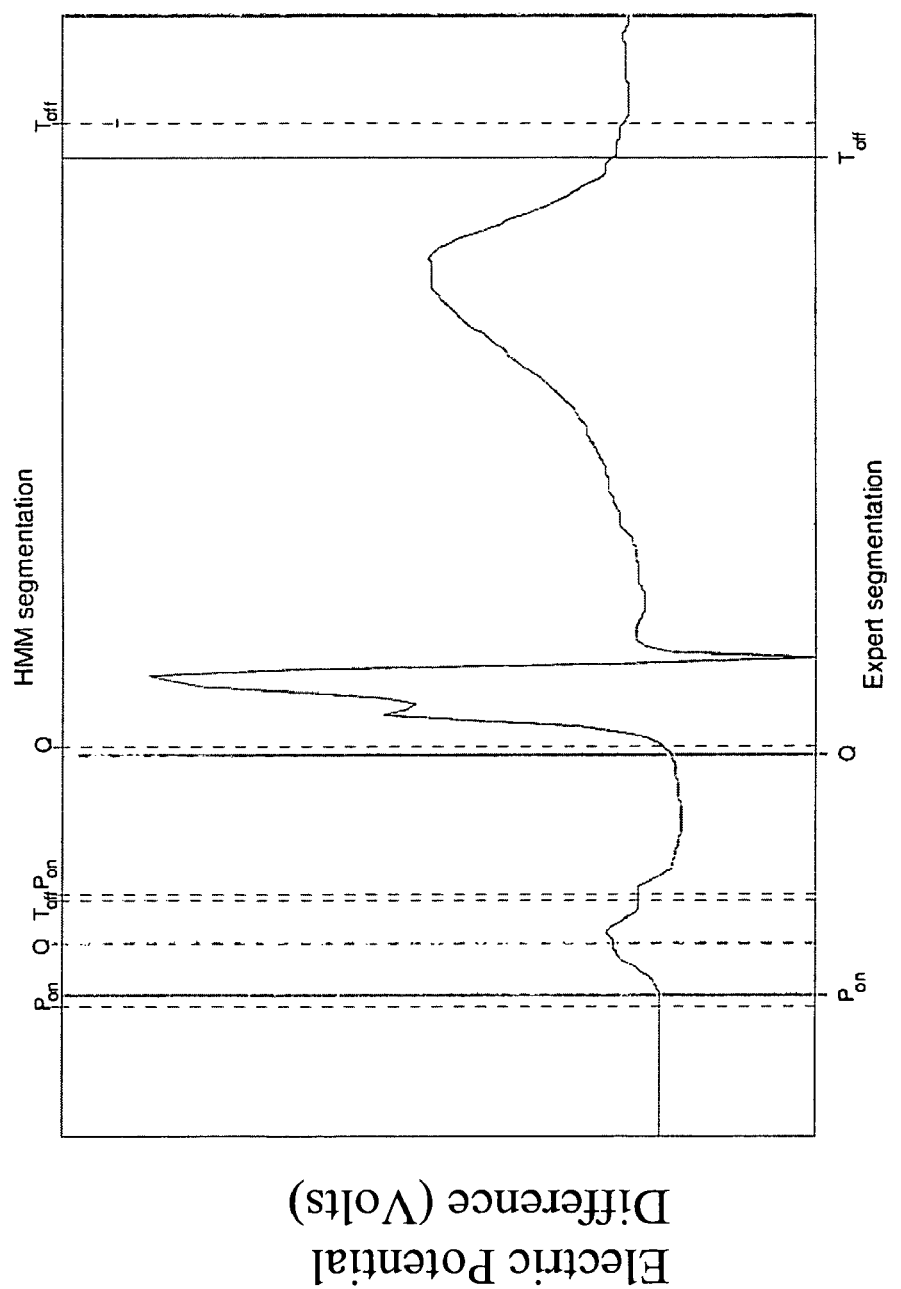
FIG. 4 shows a second ECG waveform together with the waveform boundaries as determined by an expert ECG analyst, and those inferred using a standard hidden Markov model approach.
Figure 5:
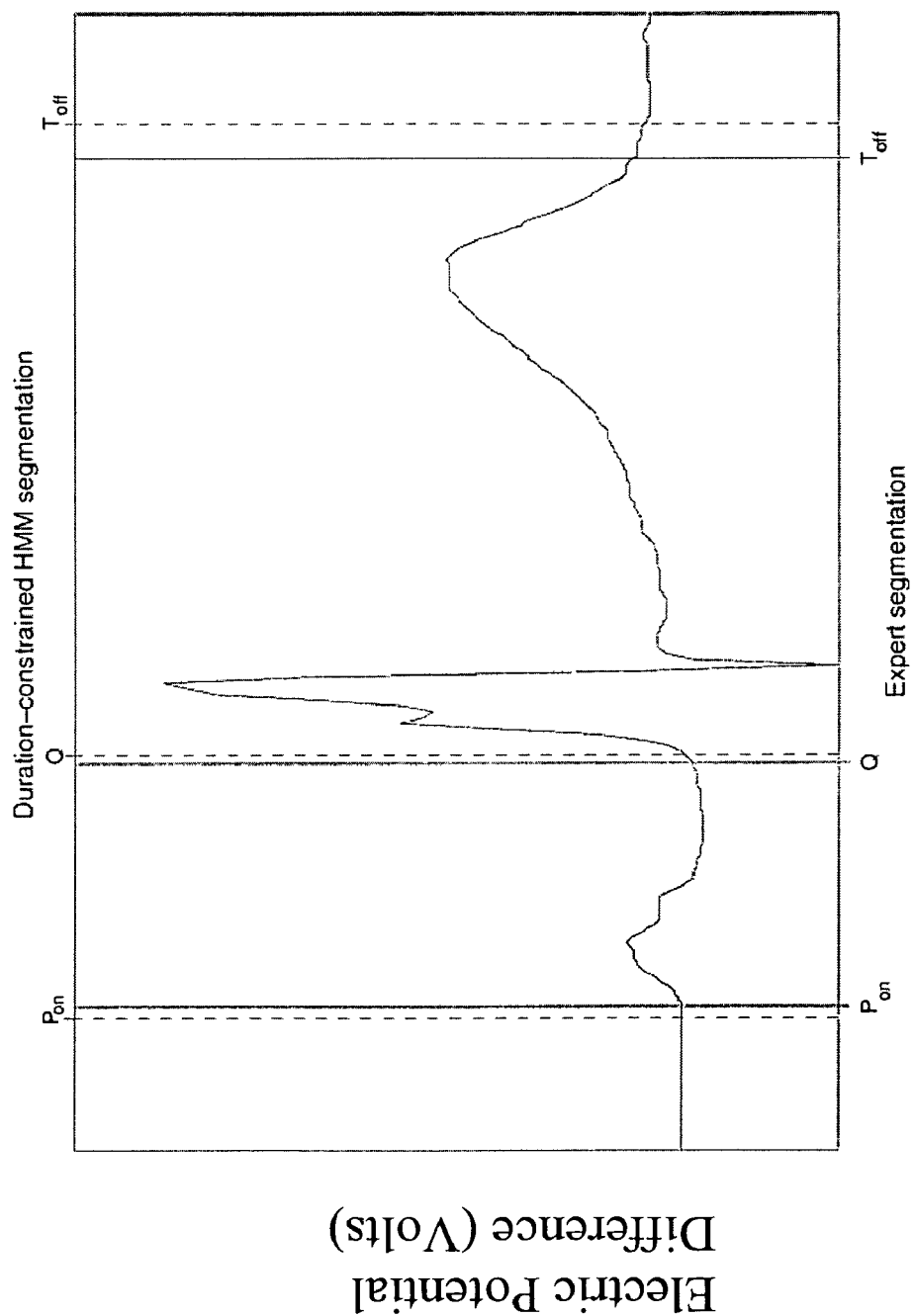
FIG. 5 shows the same ECG waveform as used in FIG. 4, together with the waveform boundaries as determined by an expert ECG analyst, and those inferred using the new duration-constrained approach.

FIGS. 3 and 5 show the same ECG waveforms as considered previously in FIGS. 2 and 4. In FIGS. 3 and 5 the waveform boundaries as determined by an expert ECG analyst are indicated by the solid vertical lines and the state boundaries determined automatically using a hidden Markov model employing duration constraints, according to an embodiment of the invention, are shown as dashed vertical lines. Not only is there good agreement between the model and the expert, but also the unreliable "double-beat" segmentation of the conventional model, as shown in FIGS. 2 and 4, has been removed, making the resulting analysis much more robust. The boundaries can be subject to further analysis, again automatically, such as determining the time duration of particular states, for example the QT interval, and statistical analysis of the variation of such intervals over a signal comprising a sequence of pulses can be performed. The results, in the form of the raw boundary information or the results of the further analysis, are output, for example by being displayed on a display of a computer system.

According to a third embodiment of the invention, in addition to the accurate segmentation of an ECG waveform, it is also possible to generate a "confidence measure" (or score) from the trained model. This confidence measure quantifies how confident the model is in the resulting segmentation, and can be used to assess the quality of the ECG waveform that has been segmented. Using this measure therefore, it is possible to automatically detect ECG waveforms that are either too noisy or too "unusual" (in terms of the waveform morphology) to provide reliable segmentations and hence reliable estimates of the QT interval. The confidence measure can be used with any segmentation algorithm which operates in a probabilistic fashion.

The confidence measure can be defined as either the log likelihood of the signal given the model, i.e. $\log p(O_1 O_2 \ldots O_T | \lambda)$, or the joint log likelihood of the signal and the most probable state sequence $s_1 s_2 \ldots s_T$ (given the model), i.e. $\log p(O_1 O_2 \ldots O_T, s_1 s_2 \ldots s_T | \lambda)$. The log likelihood, as opposed to the raw likelihood, is used in order to keep the resulting values inside the dynamic range of the computer.

Both definitions of the confidence measure can be computed efficiently for hidden Markov models and for more advanced forms of these models such as hidden semi-Markov models (as described in L. Thoraval, G. Carrault, and F. Mora, "Continuously variable durations HMMs for ECG segmentation", in *Proceedings IEEE-EMBS*, 1992, pp. 529-530) and factorial hidden Markov models (as described in Z. Ghahramani and M. I. Jordan, "Factorial hidden Markov models", in *Machine Learning*, Vol. 29, Issue 2, November 1997). The first form, which is defined as the log likelihood of the signal given the model, can be computed from the standard HMM forwards variable, given by:

$$\alpha_t(i) = p(O_1 O_2 \ldots O_t, s_t = i | \lambda)$$

It is common to scale this variable at each time step, in order to keep the resulting values inside the dynamic range of the computer. This is achieved by dividing the forwards variable by a scaling coefficient, given by:

$$c_t = \sum_{k=1}^{K} \alpha_t(i)$$

The log likelihood of the signal given the model, can then be computed simply as:

$$\log p(O_1 O_2 \ldots O_T | \lambda) = \sum_{t=1}^{T} \log c_t$$

The second form of the confidence measure, which is defined as the joint log likelihood of the signal and the most probable state sequence (given the model), can be computed from the delta variable $\delta_t(i)$, as previously described in the context of the Viterbi algorithm. It is also common to scale this variable at each time step, using a scaling coefficient given by:

$$d_t = \sum_{k=1}^{K} \delta_t(i)$$

The log likelihood of the signal and the most probable state sequence (given the model), can then be computed simply as:

$$\log p(O_1 O_2 \ldots O_T, s_1 s_2 \ldots s_T | \lambda) = \sum_{t=1}^{T} \log d_t$$

An alternative to the use of the aforementioned scaling procedure is to compute the value of $\log \alpha_t(i)$ or $\log \delta_t(i)$ directly, as described in L R Rabiner, "A Tutorial on Hidden Markov Models and Selected Applications in Speech Recognition", *Proceedings of the IEEE*, 77:257-286, 1989. In this case the confidence measures are computed directly during the recursions, and no further processing is necessary.

In many situations, the given ECG signal will contain a number of ECG features of interest (such as multiple ECG beats, or multiple QT intervals) and therefore it is desirable to compute a separate confidence measure for each individual feature of interest in the signal (rather than an aggregate measure for the entire signal). For a particular feature commencing at time sample t1 and ending at time sample t2, the confidence measure for the feature can be computed simply by subtracting the confidence measure for the section of signal upto (but not including) time t1, from the confidence measure for the section of signal upto time t2, i.e.:

$$\log p(O_1 O_2 \ldots O_{t2}|\lambda) - \log p(O_1 O_2 \ldots O_{t1-1}|\lambda)$$

or, using the second definition of the confidence measure:

$$\log p(O_1 O_2 \ldots O_{t2}, s_1 s_2 \ldots s_{t2}|\lambda) - \log p(O_1 O_2 \ldots O_{t1-1}, s_1 s_2 s_{t1-1}|\lambda)$$

When using this confidence measure in practice to assess the confidence the model has in its segmentation of a particular feature, the length of the feature in question must be taken into account during the analysis. This is necessary because both forms of the confidence measure vary with the length of the particular ECG feature.

Figure 10:
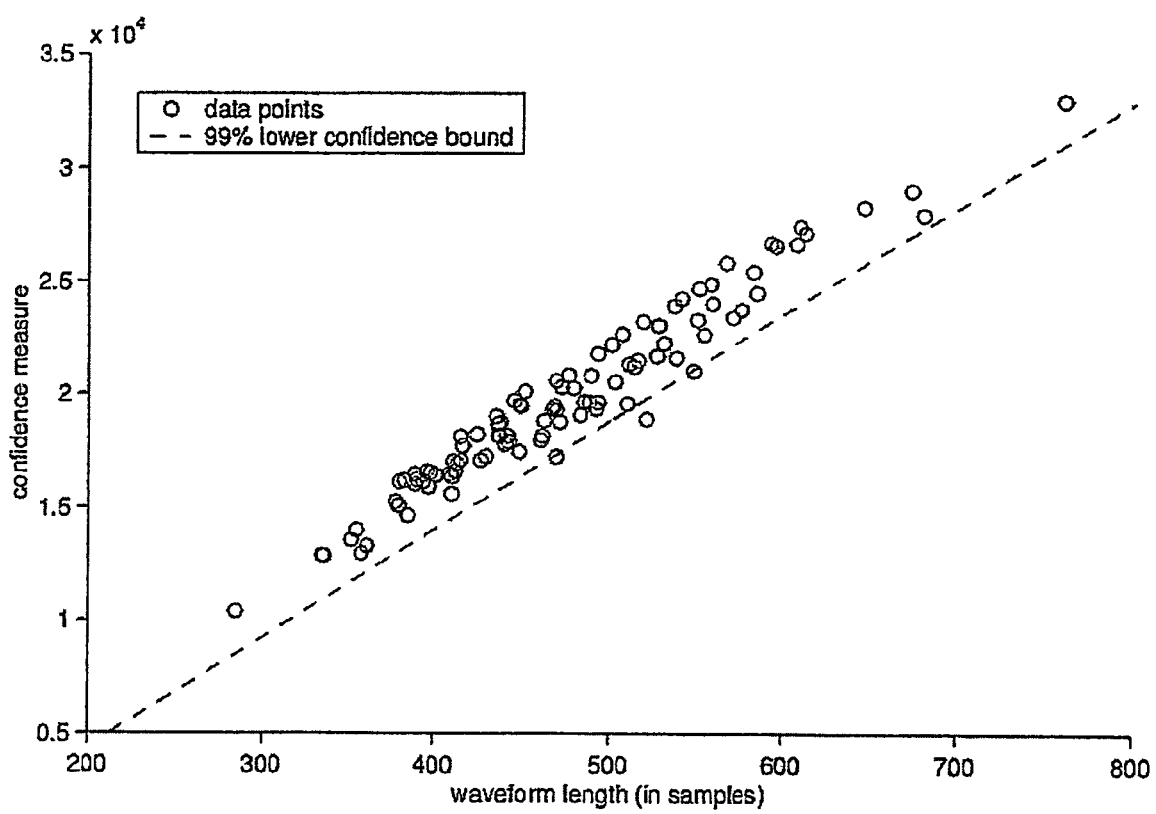
FIG. 10 shows a plot of the confidence measures against the ECG waveform lengths, for a number of regular ECG waveforms, together with the 99% lower confidence bound.

The most effective way of incorporating the length of the ECG feature into the confidence measure analysis is simply to make a plot of the confidence measure (on the y-axis) against the feature length (on the x-axis), for a large number of regular ECG features (i.e. those features which are not considered unusual, or corrupted by noise). FIG. 10 shows such a plot, where the particular feature of interest is taken to be an individual ECG waveform (i.e. the section of ECG signal corresponding to one whole heartbeat).

Given the plot of confidence measures against ECG feature lengths, it is then possible to identify a region of this 2-D space associated with high confidence features through the use of standard density modelling techniques. In particular, the set of 2-D data points corresponding to regular (i.e. high confidence) ECG features can be modelled by any suitable density function, such as a Gaussian distribution or a probabilistic linear regression model.

The given density function naturally defines a boundary for the region of high confidence in this 2-D data space. In the case of a Gaussian distribution, this boundary can be taken to be the region of the data space which lies within two standard deviations of the mean. In the case of a probabilistic linear regression model, this boundary can be taken to be region of the data space which lies above the lower confidence bound for the mean regression line at a suitable level of statistical significance (as described in R. J. Freund and W. J. Wilson, "*Regression Analysis*", Academic Press, 1998). This lower bound (at the 99% level of significance) is shown by the dashed line in FIG. 10.

Given the confidence measures for the segmentations of a number of new ECG features, together with the length of each of the segmented features, it is then a simple matter to determine if any of the confidence measures fall outside the boundary for the high confidence region. The segmentation results for those features whose confidence measure falls outside this region can then be removed from the final analysis, or alternatively these features can be highlighted for further manual analysis by a trained ECG analyst.

Figure 11:
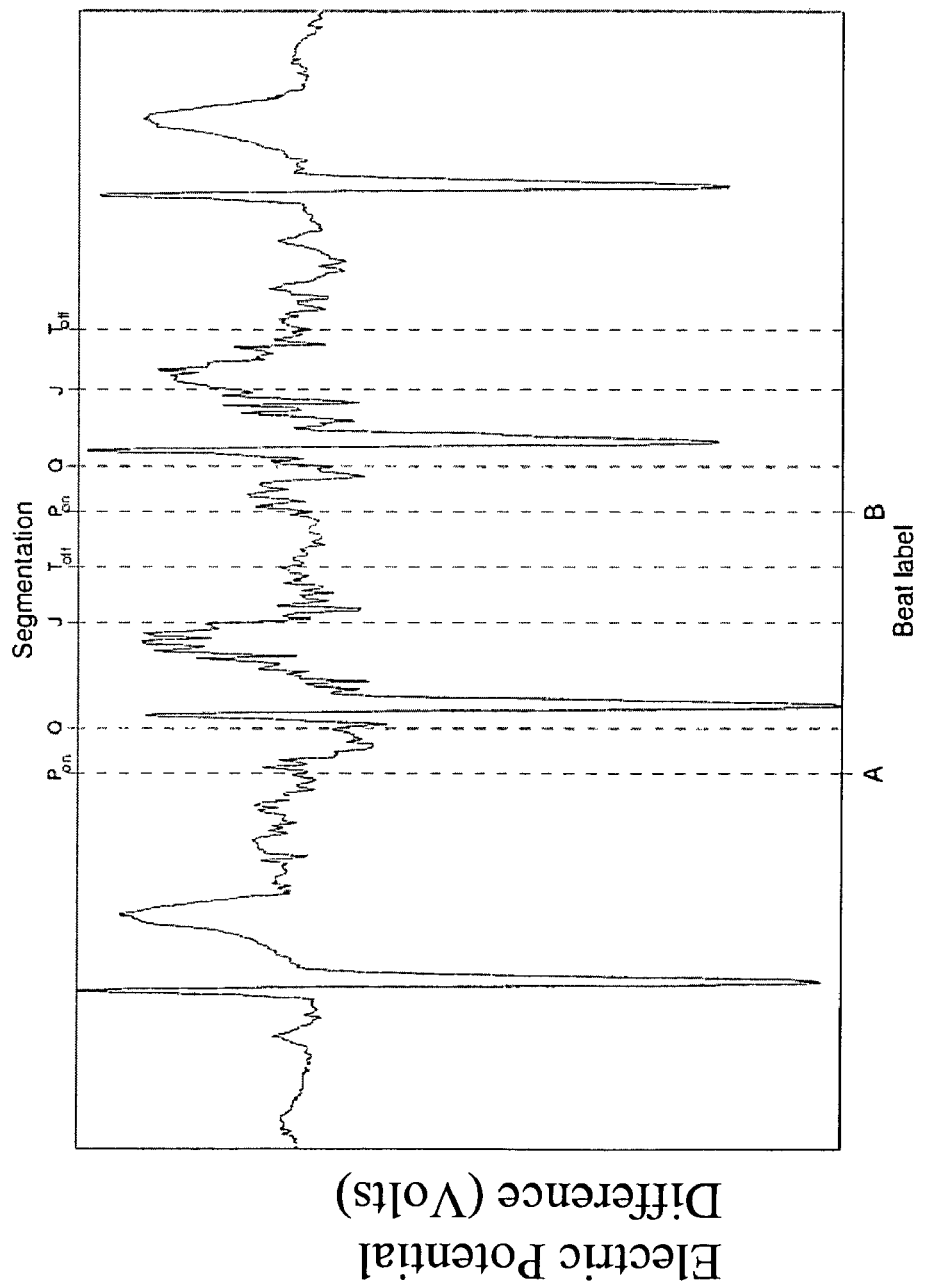
FIG. 11 shows a section of ECG signal containing two ECG waveforms corrupted by noise (in particular, "muscle artifact" noise). The segmentations of the two noisy waveforms (labelled A and B) are also shown.

FIG. 11 shows a section of ECG signal, which contains two ECG waveforms corrupted by muscle artifact noise. The figure also shows the segmentation of each waveform by a hidden Markov model with built-in duration constraints. The two waveforms are labelled "A" and "B" on the lower x-axis.

Unfortunately, the muscle artifact noise has a bandwidth similar to that of the standard ECG signal, and therefore cannot be eliminated by simple filtering techniques. The noise masks the underlying waveform features of the ECG signal, and makes the accurate segmentation of the waveforms very difficult. For this reason it is important to be able to detect such unreliable segmentations.

Figure 12:
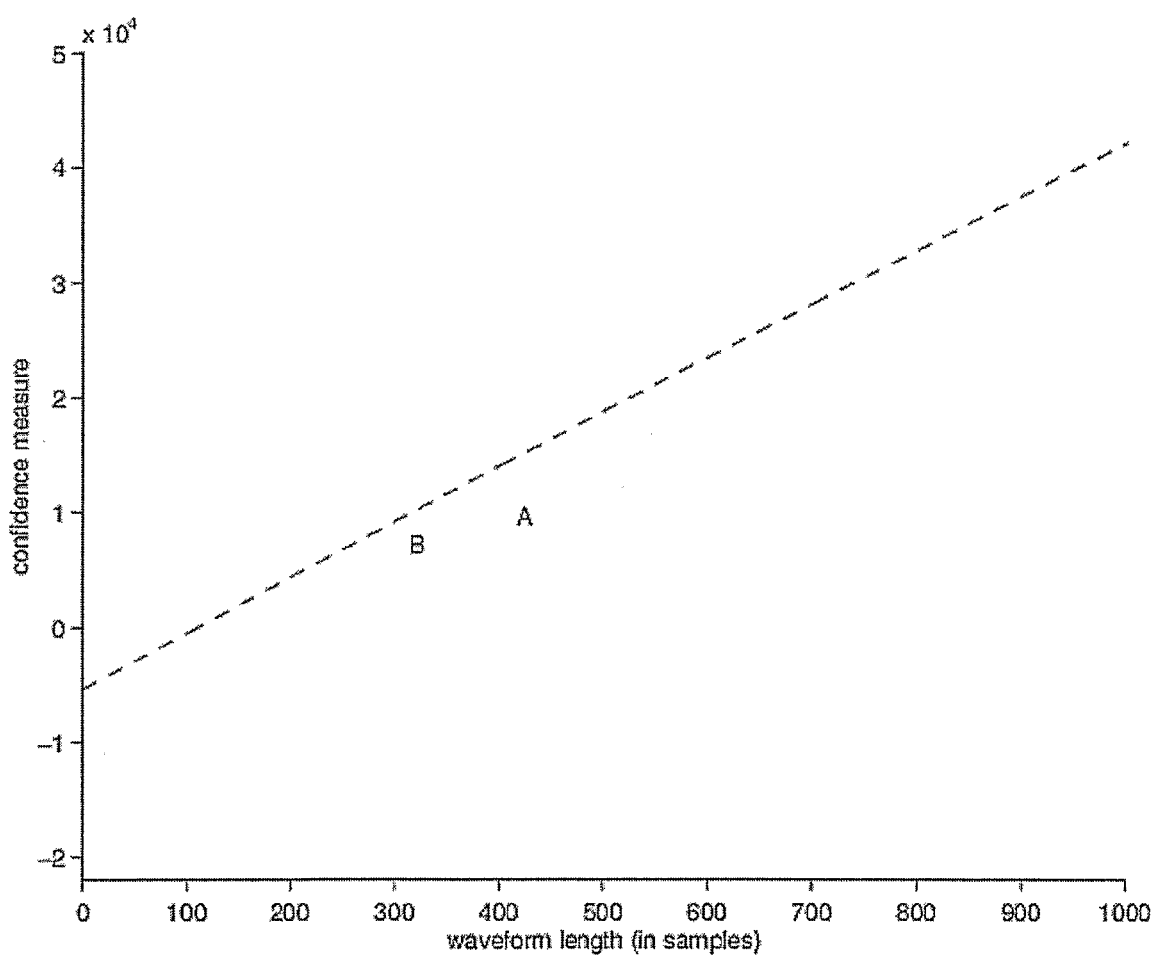
FIG. 12 shows the confidence measures for the two noisy ECG waveforms shown in FIG. 11.

FIG. 12 shows a plot of the confidence measures against the waveform lengths, for the two noisy ECG waveforms. The 99% lower confidence bound (dashed line) is also indicated. Both the confidence scores for the two noisy waveforms lie below this line, thus enabling these waveforms to be automatically detected during the automated analysis of the signal.

The above embodiments of the invention have been described in the context of ECG signal analysis. However, the invention is not limited to this application and could be used for analysis of other biomedical signals. Examples of suitable bio-medical signals include: electroencephalogram (EEG) signals, where the analysis could be used for apneoa detection; electromyogram (EMG) signals measuring electrical activity in muscles; heart signals obtained invasively such as in cardiac electrophysiology in which catheters are inserted into the heart, each catheter containing a number of electrodes; and endocardial electrogram signals, used before implantation of a pacemaker, comprising a signal derived from the heart by insertion of an electrode into the body. The duration constrained Viterbi algorithm and confidence measure technique are not limited to use with hidden Markov models. For example, the duration constrained Viterbi algorithm could be used with any finite state discrete time Markov process, and the confidence measure can be used with any segmentation algorithm which operates in a probabilistic way. The duration constrained Viterbi algorithm could be used with non biomedical signals, for example in the field of error detecting/correcting codes.

Embodiments of the invention are performed by a computer program executed on a computer system. The computer system may be any type of computer system, but is typically a conventional personal computer executing a computer program written in any suitable language. The computer program may be stored on a computer-readable medium, which may be of any type, for example: a recording medium, such as a disc-shaped medium insertable into a drive of the computer system, and which may store information magnetically, optically or magneto-optically; a fixed recording medium of the computer system such as a hard drive; or a solid-state computer memory. The signal to be analysed may be input into the computer system directly, for example from an ECG apparatus, or the computer system may read information representing the signal from a store of previously obtained signals.

The invention claimed is:

1. A computer-implemented method for analysing a signal which has been segmented using a probabilistic segmentation model, the method comprising:
   calculating a confidence measure for each of a plurality of segmented signal features;
   plotting each calculated confidence measure against a length of its respective signal feature;
   applying density modelling techniques to the plot to determine a suitable region associated with high confidence measures;
   determining whether a confidence measure for a specific signal feature falls outside this region; and
   wherein the signal is a bio-medical signal selected from the group consisting of an electrocardiogram signal, an electroencephalogram signal, an electromyogram signal, a cardiac electrophysiology signal, and an endocardial electrogram.

2. A method according to claim 1, wherein each of the plurality of segmented signal features comprise a portion of a longer signal.

3. A method according to claim 1, wherein the confidence measure is one selected from the group consisting of: the log likelihood of the signal feature given the model; and the joint log likelihood of the signal feature and the most probably state sequence given the model.

4. A method according to claim 1, further comprising displaying the plot of each calculated confidence measure against the length of its respective signal feature.

5. A method according to claim 1, wherein the signal is an electrocardiogram signal and information on a QT interval is obtained from the probabilistic segmentation model.

6. A non-transitory computer-readable medium storing a computer program capable of being executed on a computer system and capable when so executed of causing the computer system to perform a method according to claim 1.

* * * * *